(12) United States Patent
Rho et al.

(10) Patent No.: US 8,273,718 B2
(45) Date of Patent: Sep. 25, 2012

(54) COMPOSITION FOR PREVENTION OR TREATMENT OF BONE METABOLISM DISORDER COMPRISING D-PINITOL AS AN ACTIVE INGREDIENT

(75) Inventors: Jaerang Rho, Daejeon (KR); Hyeon-Koon Myeong, Daejeon (KR)

(73) Assignee: Solgent Co., Daejeon (KR)

( * ) Notice: Subject to any disclaimer, the term of this patent is extended or adjusted under 35 U.S.C. 154(b) by 206 days.

(21) Appl. No.: 12/676,481

(22) PCT Filed: Sep. 3, 2008

(86) PCT No.: PCT/KR2008/005192
§ 371 (c)(1),
(2), (4) Date: Apr. 5, 2010

(87) PCT Pub. No.: WO2009/031819
PCT Pub. Date: Mar. 12, 2009

(65) Prior Publication Data
US 2010/0210733 A1   Aug. 19, 2010

(30) Foreign Application Priority Data
Sep. 5, 2007   (KR) .................. 10-2007-0090073

(51) Int. Cl.
*A61K 31/70* (2006.01)
(52) U.S. Cl. ............................................................ 514/23
(58) Field of Classification Search ..................... 514/23
See application file for complete search history.

(56) References Cited

FOREIGN PATENT DOCUMENTS

| | | |
|---|---|---|
| EP | 1 241 155 A1 | 9/2002 |
| KR | 10-2005-0111667 | 11/2005 |
| WO | WO 91/09601 | 7/1991 |
| WO | WO 96/29063 | 9/1996 |
| WO | WO 2004/084875 A1 | 10/2004 |

OTHER PUBLICATIONS

International Search Report from International Application No. PCT/KR2008/005192, dated Mar. 24, 2009 (date of completion of search) and Mar. 25, 2009 (date of mailing of report).

*Primary Examiner* — Raymond Henley, III
(74) *Attorney, Agent, or Firm* — Clark & Elbing LLP (57) ABSTRACT

The present invention provides a composition for inhibiting osteoclastogenesis and a pharmaceutical composition for preventing or treating a bone metabolism disorder, which comprise D-pinitol as an active ingredient. The present compositions have an inhibitory activity on the differentiation of osteoclast and are useful in the prevention or treatment of a bone metabolism disorder resulting from overactivity or hyper-proliferation of osteoclasts.

2 Claims, 13 Drawing Sheets

COMPOSITION FOR PREVENTION OR TREATMENT OF BONE METABOLISM DISORDER COMPRISING D-PINITOL AS AN ACTIVE INGREDIENT

CROSS-REFERENCE TO RELATED APPLICATIONS

This application is the U.S. national stage filing under 35 U.S.C. §371 of international application PCT/KR2008/005192, filed Sept. 3, 2008, which claims priority from Korean Patent Application 10-2007-0090073, filed Sept. 5, 2007.

BACKGROUND OF THE INVENTION

1. Field of the Invention

The present invention relates to a composition for prevention or treatment of a bone metabolism disorder comprising D-pinitol as an active ingredient.

2. Background of Technique

Bone supports muscles or organs of human body and protects internal organs from external impact by surrounding them. Bone is also an important part of human body, which stores not only internal calciums but also essential inorganic substances such as phosphorus or magnesium. Old bone matrix of adult is removed and replaced with new one. The balance of bone production is maintained through the repeated process of a resorption and destruction. This process is named as bone remodeling (Yamaguchi A. et al., *Tanpakushitsu Kakusan Koso*, 50(6 Suppl):664-669 (2005)). Turnover of bone matrix may be essential to the recovery of a subtle injury of bone generated by stress and bone growth, and to suitable maintenance of bone function (Cohen-Solal M. et al., *Therapie*, 58(5):391-393 (2003)).

It is known that two types of cells are associated with bone remodeling. One is osteoblast which is in charge of building bone and the other is osteoclast in charge of destroying it. The osteoblast produces RANKL (receptor activator of nuclear factor-κB ligand) and its decoy receptor, OPG (osteoprotegerin). Where RANKL is bound to RANK (receptor activator of nuclear factor-κB) on osteoclast progenitor cells, osteoclast progenitor cell become matured to osteoclast, allowing bone resorption to be occurred. However, when OPG is bound to RANKL, the binding of RANKL to RANK is blocked and resulted in the prevention of osteoclast formation and inhibition of bone resorption (Theill L E. et al., *Annu Rev Immunol*, 20:795-823 (2002); Wagner E F. et al., *Curr Opin Genet Dev*, 11:527-532 (2001)). Resorption or destruction of old bone is carried out by osteoclast derived from blood cell (hematopoietic stem cell), which gnaw a hole on bone and release a small amount of calcium into blood flow. The released calcium can be used to maintain the body function (William J. et al., *Nature*, 423:337-342 (2003)).

Figure 1:
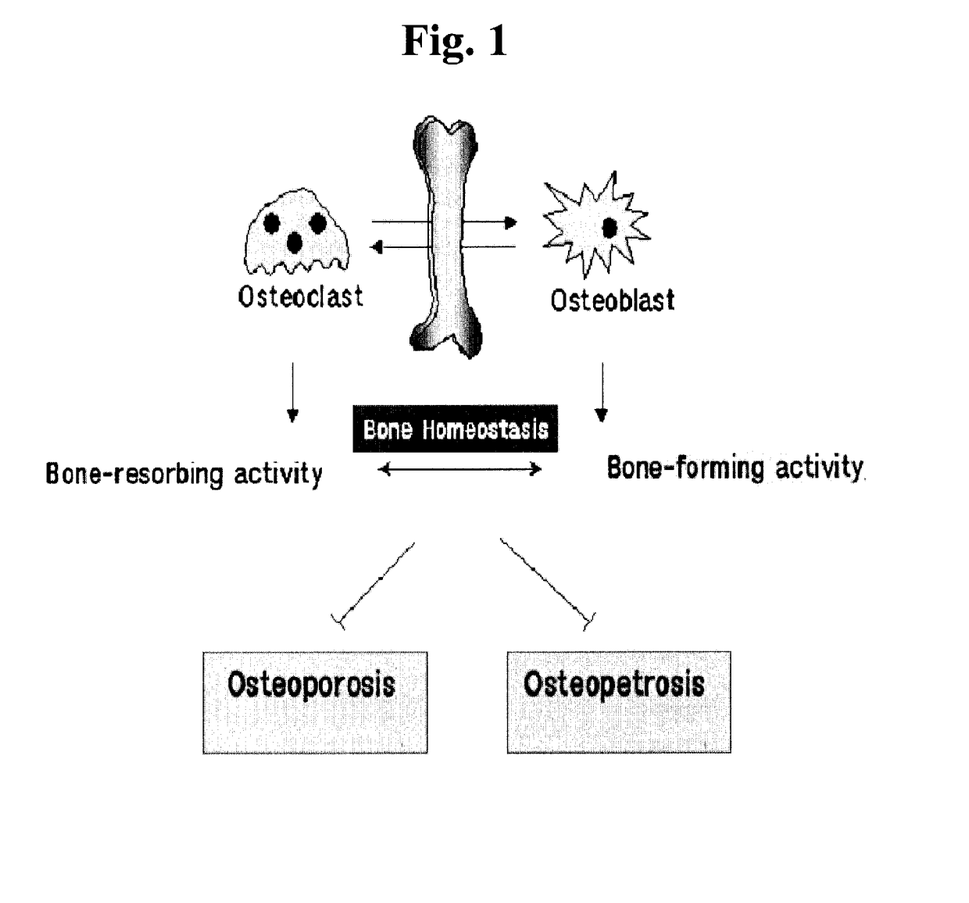
FIG. 1 schematically represents homeostasis regulation of osteoclast and osteoblast and pathogenesis mechanism of osteoporosis.

Osteoblast can reconstruct skeleton by generating rigid new bone through the process of filling the hole on bone with collagen and covering it with hydroxyapatite of calcium and phosphorus (Stains J P. et al., *Birth Defects Res C Embryo Today*, 75(1):72-80 (2005)). In order to maintain constant bone density, the rate of osteoclastic destruction must be same with the osteogenetic rate of bone. When the balance of bone remodeling is broken, various diseases, for example osteoporosis may be occurred (FIG. 1).

Osteoporosis is a disorder in which bone mass is reduced by various causes and the risk of bone fracture continuously increase due to the degeneration of microstructure on bone tissue. Osteoporosis is a condition in which the content of minerals (e.g., calcium) and substrates of bone has been reduced. Osteoporosis can be occurred when the activity of osteoclasis becomes superior to that of osteogenesis owing to the imbalance of bone remodeling (Iqbal M M., *South Med J*, 93(1): 2-18 (2000)).

The patient of osteoporosis is characterized by the rapid bone loss (2-3% per a year) at the time of the beginning of menopause. Osteoporosis is classified into two types of disease according to its cause: a postmenopausal osteoporosis in which spinal pressure and fracture risk of carpal bone are increased and secondary osteoporosis which is generated from various age-irrelevant causes such as diseases (endocrinopathy, gastrointestinal disorder, malignant tumor), drugs (adrenocortical hormone, anticancer chemotherapy, thyroid hormone, anticonvulsant, anticoagulant, methotexate, cyclosporine, GnRH, etc.), alcohol, smoking and accident (Rosep C J., *N Eng J Med*, 353(6):595-603 (2005); Davidson M., *Clinicain Reviews*, 12(4):75-82 (2002)).

Therapeutic agents for osteoporosis that act via suppressing the function of osteoclast are currently developed in two directions. The first is to develop an agent inhibiting the bone resorption process of osteoclast. A substance that can prevent the bone resorption process of differentiated osteoclasts may be directly used as a therapeutic agent of osteoporosis. The second is to investigate a substance that can inhibit the signal transduction pathway of osteoclastogenesis.

Figure 2:
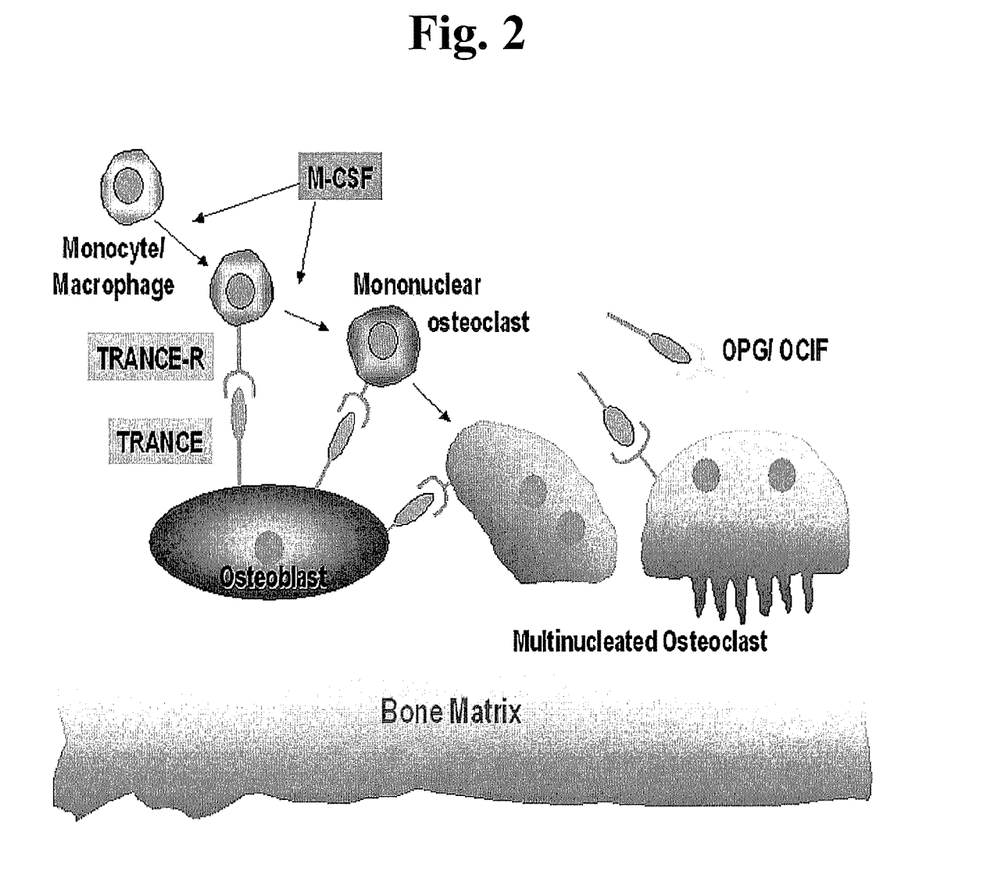
FIG. 2 schematically represents osteoclastogenesis and function of cytokines associated with it.

Osteoclast is differentiated from hematopoietic stem cells which reside in bone marrow like the differentiation of immune cells. Osteoclast is initially differentiated to monocyte by macrophage differentiation factors, M-CSF (macrophage-colony stimulating factor) and TRANCE (TNF-related activation induced cytokine), and finally to osteoclast by TRANCE (FIG. 2) (1-6).

Another important disease caused by the disruption of a bone remodeling balance is a bone injury due to the metastasis of cancer cells to bone. Metastasis to bone is almost always occurred in patents having breast cancer, prostate cancer or multiple myeloma (Kozlow W. et al., *J Mammary Gland Biol Neoplasia*, 10(2):169-180 (2005)). It is known that the survival period of these cancer patients depends on the occurrence of cancer metastasis to bone.

The Metastasis to bone observed in breast cancer patients is osteolytic metastasis in which most of bone is destroyed and is known to be occurred by stimulating the osteoclast not by direct action of breast cancer cell (Boyde A. et al., *Scan Electron Microsc*, 4:1537-1554 (1986)). On the other hand, metastasis to bone observed in prostate cancer is osteoblastic metastasis. It is also known that osteoblsatic metastasis has a close relation with osteolysis.

D-pinitol is known to be contained in pinewood and legumes. A pinitol-like substances of undisclosed structure extracted from Bougainvillea spectabilis was found to lower the blood glucose level of both normal and alloxan-treated insulin-deficient mice at a minimum dosage of 0.01 g/kg (Narayanan, C. R., Joshi, D. D., Mujumdar, A. M., Dhekne, V. V. 1987. Pinitol—A new antidiabetic compound from the leaves of Bougainvillea spectabilis. Current Science 56: 139141). U.S. Pat. No. 5,827,896 proposed use of D-pinitol and its derivatives in diabetes treatment as metabolism disorder. However, it has not been known yet that D-pinitol has efficacy of treatment for diseases associated with bone.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a substance that can be used for effectively preventing or treating a bone metabolism disorder and at the same time applied to human body for a long period with safety. As results, we have discovered that D-pinitol has a remarkable activity to inhibit the formation and differentiation of osteoclast and is able to be used as an agent for treating or preventing the bone metabolism disorders by improving the imbalance of a bone metabolism.

Accordingly, it is an object of this invention to provide a composition for inhibition of osteoclastogenesis, which comprises D-pinitol as an active ingredient.

It is another object of this invention to provide a functional food composition or pharmaceutical composition for improvement, prevention or treatment of a bone metabolism disorder, which comprises D-pinitol as an active ingredient.

It is still another object of this invention to provide a method for prevention or treatment of a bone metabolism disorder.

It is still another object of this invention to provide a use of D-pinitol to prepare a medicament for prevention or treatment of a bone metabolism disorder.

Other objects and advantages of the present invention will become apparent from the following detailed description together with the appended claims and drawings.

In one aspect of this invention, there is provided a composition for inhibition of osteoclastogenesis, which comprises D-pinitol as an active ingredient.

The present inventors have made intensive studies to develop a substance that can be used for effectively preventing or treating a bone metabolism disorder and at the same time applied to human body for a long period with safety. As results, we have discovered that D-pinitol has a remarkable activity to inhibit the formation and differentiation of osteoclast and is able to be used as an agent for treating or preventing the bone metabolism disorders by improving the imbalance of a bone metabolism.

The present inventors demonstrated that D-pinitol has an activity to inhibit the differentiation process from osteoclast progenitor cells to osteoclast. Thus, the present composition comprising D-pinitol as an active ingredient may be effectively used as an agent to inhibit osteoclastogenesis.

In another aspect of this invention, there is provided a pharmaceutical composition for prevention or treatment of a bone metabolism disorder, which comprises (a) a therapeutically effective amount of D-pinitol; and (b) a pharmaceutically acceptable carrier.

In still another aspect of this invention, there is provided a functional food composition for prevention or improvement of a bone metabolism disorder, which comprises D-pinitol as an active ingredient.

In still another aspect of this invention, there is provided a method for prevention or treatment of a bone metabolism disorder comprising administrating to a subject suffering from the bone metabolism disorder a pharmaceutical composition which comprises (a) a therapeutically effective amount of D-pinitol; and (b) a pharmaceutically acceptable carrier.

It is still another object of this invention to provide a use of D-pinitol to prepare a medicament for prevention or treatment of a bone metabolism disorder.

The "D-pinitol" as an active compound of this invention has the chemical structure given below.

The term "D-pinitol" as used herein includes a "D-pinitol-like compound" which has an inhibitory activity on osteoclastogenesis equal to D-pinitol.

As used herein, the term "D-pinitol-like compound" includes a suitable derivative or metabolite of D-pinitol, a compound containing D-pinitol or a prodrug of D-pinitol.

A suitable "derivatives" or "metabolites" of D-pinitol as used herein include, but are not limited to, D-pinitol glycosides, D-pinitol phospholipids, esterified D-pinitol, lipid-bound D-pinitol, D-pinitol phosphate, D-pinitol phytates and combination thereof.

As used herein, the term "compound containing D-pinitol" refers to any compound that contains the D-pinitol moiety as part of a larger structural composition. The "compound containing D-pinitol" includes, but is not limited to, polysaccharides comprising D-pinitol and one or more additional sugars (glucose, galactose, mannose, glucosamine, galactosamine and mannitol) and complexes or chelates of D-pinitol with one or more metal ions.

The term "prodrug" as used herein denotes a derivative of D-pinitol that is converted to D-pinitol in vivo by an enzymatic or chemical process but exhibits enhanced delivery characteristics and/or therapeutic value. The preparation and administration of prodrugs of saccharides, for example in the form of methylated or acetylated hydroxyl groups, is well known in the art (Baker et al., *J. Med. Chem,* 27:270-274 (1984)).

D-pinitol is available from a number of natural sources, for example pine needles, chick peas, Bougainvillea leaves, alfalfa, soy beans and other legumes, or synthetic processes and preferably from soy beans fractions.

As used herein, the term "osteoclast" refers to a cell responsible for destruction of bone in bone remodeling process in which old bone matrix is substituted with new bone matrix.

The D-pinitol as an active ingredient of the pharmaceutical composition has an activity to inhibit the differentiation and formation process of osteoclasts from osteoclast progenitor cells.

Accordingly, the present composition can be effectively used for preventing or treating bone metabolism disorders.

As used herein, the term "bone metabolism disorders" refers to disorders or diseases which are caused from unbalance of activity or proliferation between osteoclast and osteoblast, for example diseases or conditions resulted from overactivity or hyper-proliferation of osteoclast. The term "diseases or conditions resulted from overactivity or hyper-proliferation of osteoclast" means diseases generated from the state of osteoclasts being excessively activated or proliferated.

The term "prevention" as used herein refers to the prevention of diseases or disorders from occurring in an animal which may be predisposed to the diseases or disorders but has not yet been diagnosed as having them. The term "treatment" refers to (i) an inhibition of development of diseases or disorders; (ii) an alleviation of diseases or disorders; and (iii) an elimination of diseases or disorders.

According to another preferable embodiment, the present composition may be used for the improvement, prevention or treatment of disorders caused from the excessive bone resorption by osteoclast.

According to still another preferable embodiment, the present composition can be used for preventing or treating osteoporosis and related osteopenic diseases.

Diseases to be treated, prevented or improved by the present composition include osteoporosis, particularly osteoporosis associated with a peri or post menopausal period, Paget's disease, hypercalcemia associated with bone neoplasms and other types of osteoporotic disease and related disorders including but not limited to: involutional osteoporosis, Type I or postmenopausal osteoporosis, Type II or senile osteoporosis, juvenile osteoporosis, idiopathic osteoporosis, endocrine abnormality, hyperthyroidism, hypogonadism, ovarian agenesis or Turner's syndrome, hyperadrenocorticism or Cushing's syndrome, hyperparathyroidism, bone marrow abnormalities, multiple myeloma and related disorders, systemic mastocytosis, disseminated carcinoma, Gaucher's disease, connective tissue abnormalities, osteogenesis imperfecta, homocystinuria, Ehlers-Danlos syndrome, Marfan's syndrome, Menke's syndrome, immobilization or weightlessness, Sudeck's atrophy, chronic obstructive pulmonary disease, chronic heparin administration and chronic ingestion of anticonvulsant drugs.

The present composition is also used for, but is not limited to, treatment or prevention of rheumatoid arthritis, peridontal disease, periprosthetic osteolysis, other autoimmune diseases, neoplastic destruction of bone, and bone resorption disorders associated with cancer.

It will be also appreciated that the present composition may be used for the treatment of other disorders and secondary conditions resulted from overactivity or hyper-proliferation of osteoclasts that are not specifically listed herein.

According to the most preferable embodiment, other disorders resulting from overactivity or hyper-proliferation of osteoclasts include osteoporosis, Paget's disease, hypercalcemia, rheumatoid arthritis, metastatic bone destruction, cancer and immune diseases.

The present phamarceutical composition for prevention or treatment of disorders resulting from overactivity or hyper-proliferation of osteoclasts also includes a pharmaceutically acceptable carrier besides an active ingredient.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.001-1000 mg/kg (body weight).

The pharmaceutical composition according to the present invention may be administered via the routes used commonly and preferably, administered parenterally, i.e., by intravenous, intraperitoneal, intramuscular, subcutaneous, or local administration. It is preferable that administration route of the pharmaceutical composition is determined by the types of diseases.

The concentration of D-pinitol as an active ingredient to be contained in this composition may be determined depending on the purpose of treatment, patient's conditions, period of necessity, severity of diseases, but be not limited to a particular range of concentration.

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The present composition may be prepared to provide a food composition, in particular a functional food composition. The food composition may comprise conventional additives for preparing food compositions, e.g., proteins, carbohydrates, lipids, nutritive substances and flavors. For example, where the food composition of this invention is provided as a drink, it may further comprise flavors and natural carbohydrates as well as D-pinitol as an active ingredient. Non-limiting examples of natural carbohydrates include, but not limited to, monosaccharide (e.g., glucose and fructose), disaccharide (e.g., maltose and sucrose), oligosaccharide, polysaccharide (e.g., dextrin and cyclodextrin) and sugar alcohol (e.g., xylitol, sorbitol and erythritol). Non-limiting examples of flavors include, but not limited to, natural flavors (e.g., thaumatin and extract of Stevia) and synthetic flavors (e.g., saccharin and aspartame). Considering availability to foods, the food composition of this invention is very useful in preventing, treating, or improving bone metabolism disorders.

The present invention will now be described in further detail by examples. It would be obvious to those skilled in the art that these examples are intended to be more concretely illustrative and the scope of the present invention as set forth in the appended claims is not limited to or by the examples.

EXAMPLES

Methods
Culture of Raw264.7 Cells and Differentiation of Osteoclasts

Raw264.7 cells were cultured in α-MEM (α-minimal essential medium) containing 10% FBS (fetal bovine serum). In the experiment of examining osteoclastogenesis, cells were adjusted to $2.0 \times 10^3$ cells/200 μl on 96-well plate and incubated with 200 ng/ml of sRANKL. TRAP (tartrate resistant acid phophatase) staining and TRAP solution assay were carried out at forth day after culturing cells for 3 days with treatment of D-pinitol at concentrations of 1, 3.5, 7, 12.5, 25 and 50 mM respectively. Cells were fixed for TRAP staining and TRAP solution assay. TARP positive multinuclear (more than 3 nuclei) cells were counted as an osteoclast-like cell. Cells were observed using Leica DM IRM microscope.

TRAP Staining

For cytochemical staining of TRAP positive cell, medium was removed. After that, 100 μl of 10% formalin was added to cells and incubated for 10 min at room temperature. 100 μl of methanol/acetone was added and incubated for 1 min at room temperature. Cells were stained with 10 ml of TRAP buffer (Tris-HCl, pH 4.5, EDTA), naphthol AS phosphate (substrate, Sigma #N-4875) and 5 mg of Fast Red Violet dye (Sigma, F-1625). 1 mg of naphthol AS phosphate dissolved in 150 ml of N, N-dimethyl formide (DMF, Sigma #319937) was used. The reaction was performed for 10-30 min and then red color was observed. Where red color is clearly observed, it was washed with flowing water and dried. TRAP-stained cells were observed in light microscope.

TRAP Solution Assay

TRAP solution assay of TRAP positive cells were carried out according to the following method. Medium was removed, 100 μl of 10% formalin was added and incubated for 10 min at room temperature. After 100 μl of methanol/acetone was added, incubated for 1 min at room temperature, and then dried. TRAP substrate solution comprising a tablet of pNPP (p-nitrophenylphosphate) dissolved in 20 ml of TRAP buffer (pH 5.2) was added into and incubated for 20-30 min at 37° C. 100 μl of TRAP substrate solution was transferred to a new 96-well plate in which 50 μl of 1N NaOH was contained. Finally, OD (optical density) value was measured at 405 nm.

Cytotoxicity Analysis of D-pinitol

To verify the cytotoxicity of D-pinitol to Raw264.7 cell, Raw264.7 cells were grown on 96-well plate until $0.5 \times 10^3$ cells/200 μl. Cells were cultured for 3 days while treating with D-pinitol at concentrations of 1, 3.5, 7, 12.5, 25 and 50 mM respectively. Cell number increased during 3 days of culture was counted to determine the cytotoxicity of added compounds.

To investigate the cytotoxicity of D-pinitol to a bone marrow cell, bone marrow cells were adjusted to $1.0 \times 10^5$ cells/200 μl on 96-well plate and co-cultured with 50 ng/ml of M-CSF. Then, cultured cells were grown for 4 days while treating with D-pinitol at concentrations of 1, 3.5, 7, 12.5, 25 and 50 mM respectively. Cytotoxicity was measured using CCK8 kit (Cell Counting Kit-8, Dojindo, Japan). 10% CCK8 solution was added to culture solutions according to each culture time and incubated for 2 hrs at 37° C. After culturing, an absorbance was measured at 450 nm using Microplate reader (Bio-Rad).

Effect of D-pinitol on Differentiation of Bone Marrow-Derived Osteoclast

To extract mouse bone marrow cells, thighbone and shinbone of male C57BL/6 mouse at 3-4 weeks of age were aseptically enucleated and their soft tissues were eliminated. Both end of long bone was cut in extracted bone tissues and then bone marrow cells were collected by injecting α-MEM/10% FBS into bone marrow cavity at one end using a 26G injection syringe. Collected bone marrow cells were subjected to 5 ng/ml of M-CSF and incubated for 16 hrs. Unattached cells on plate bottom were harvested.

For the induction of the differentiation of bone marrow-derived osteoclast, bone marrow cells of $1.0 \times 10^5$ cells per well were cultured with α-MEM/10% FBS in the presence of 200 ng/ml of sRANKL and 50 ng/ml of M-CSF. D-pinitol was added to media at various concentrations during culture. Three experiments were carried out at each concentration and media were replaced at third day after grown in complete media containing sRANKL, M-CSF and D-pinitol. Cells were observed in Leica DM IRM microscope at forth day and then TRAP staining and TRAP solution assay were carried out.

To examine the effect of D-pinitol on osteoclast at each stage of culturing, D-pinitol was added to the culture media of osteoclast with various concentrations. D-pinitol-treated osteoclast was separated at each cultured time and then amount of differentiated osteoclast was analyzed using TRAP solution assay.

Osteoblast Preparation and Co-culture with Osteoclast

To prepare a primary osteoblast of mice, frontal bone and parietal bone of fetal mice at 1 day of age were aseptically enucleated. After washing enucleated bone tissue with PBS solution, it was subsequently treated with mixed-enzyme solution (0.2% collagenase and 0.1% dispase) 6 times at 20 min intervals. Cells having the property of osteoblast were harvested and then washed with culture solution. Washed cells were cultured in α-MEM containing 10% serum for 3 days and used as a primary osteoblast. Co-culture was carried out in a manner that $1.0 \times 10^4$ cells/200 μl of osteoblast and $1.0 \times 10^5$ cells of bone marrow cells were cultured on 96-well plate with vitamin $D_3$ ($10^{-6}$M) and prostagrandin $E_2$ (PGE2, $10^{-8}$M) for 5 days. After culturing, TRAP staining was performed.

Measurement of Degradative Potential of Osteoclast in Bone Resorption Process

To examine the effect of D-pinitol on degradative potential of osteoclast in the bone resorption process, fragment of tooth bone was added in 96-well plate and then bone marrow cells were cultured until $1.0 \times 10^5$ cells/200 μl. For the differentiation of osteoclast, 50 ng/ml of M-CSF and 200 ng/ml of sRANKL were added. D-pinitol was added to the media in a concentration-dependent manner and incubated for 4 days. Where the differentiation of osteoclast was observed after completing the culture, cells were removed in bone fragment and observed in microscope via 1% toluidine blue staining.

Results

Cytotoxicity of D-pinitol on Raw264.7 Cells

Figure 3:
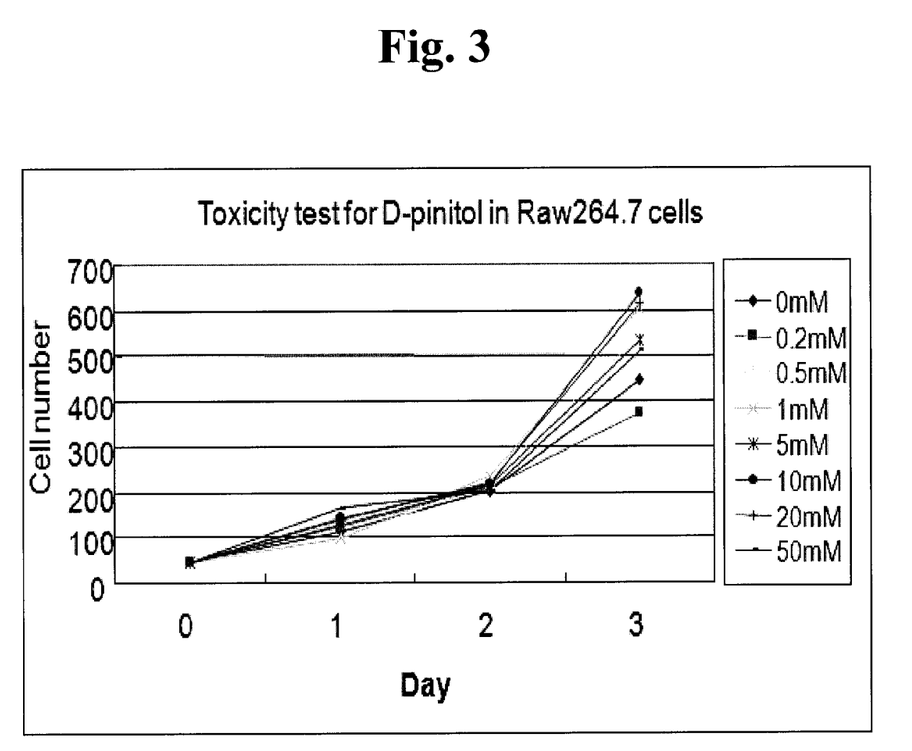
FIG. 3 is a graph showing the effect of D-pinitol on proliferation of Raw 264.7 cell. Cell number was measured for 3 days at 24 hrs intervals after treating D-pinitol at concentrations of 0, 0.2, 0.5, 1, 5, 10, 20 and 50 mM.

The present inventors examined the cytotoxicity of D-pinitol at various concentrations. Influence of D-pinitol to cell proliferation was examined by treating Raw264.7 cells with various concentrations of D-pinitol. Osteoclast progenitor cell line, Raw264.7 cells were cultured and treated with D-pinitol in a range of 0-50 mM concentration. The number of survived cells was counted for 3 days at 24 hrs intervals. As shown in FIG. 3, it could be understood that Raw264.7 cell cytoxicity was not observed even at a maximum concentration of 50 mM D-pinitol.

Cytotoxicity of D-pinitol on Hematopoietic Stem Cells

Figure 4:
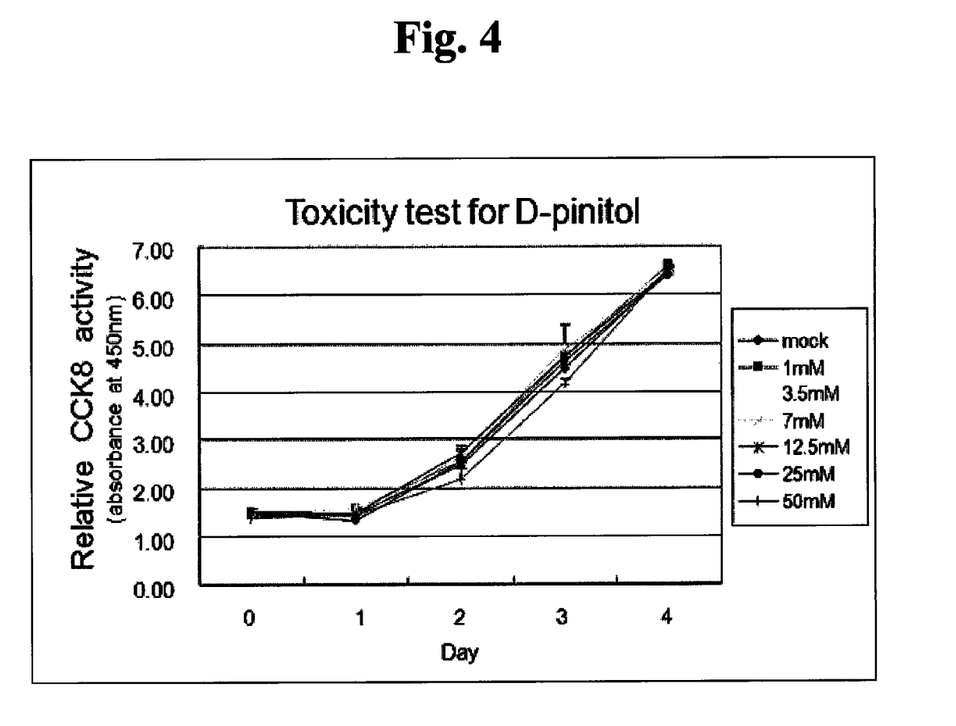
FIG. 4 is a graph showing the concentration-dependent effects of D-pinitol on bone marrow-derived hematopoietic stem cell proliferation.

The instant inventors examined the cytotoxicity of D-pinitol on hematopoietic stem cells. Hematopoietic stem cells were extracted from bone marrow and then the proliferation of cells was induced by treating with M-SCF (50 ng/ml). After that, the proliferation-induced cells were treated with D-pinitol at a range of 0-50 mM and the effect of D-pinitol on cell proliferation was determined by measuring CCK8 enzyme activity. As shown in FIG. 4, D-pinitol had no effect on CCK8 activity in the range of 0-50 mM. D-pinitol of not more than 50 mM had no influence on the proliferation of hematopoietic stem cells.

Inhibitory Activity of D-pinitol on Osteoclastogenesis of Raw264.7 Cell—TRAP Staining Raw264.7 cells begin to differentiate into osteoclast when cellular signal transduction is initiated by RankL. Fusion between cells is occurred in an early stage of differentiation. When differentiation is finished, osteoclast becomes multinucleate cell having 2-50 nuclei. Formation of multinucleate cell is a typical property related to the differentiation of osteoclast. Osteoclastogenesis may be confirmed by TRAP staining.

Figure 5:
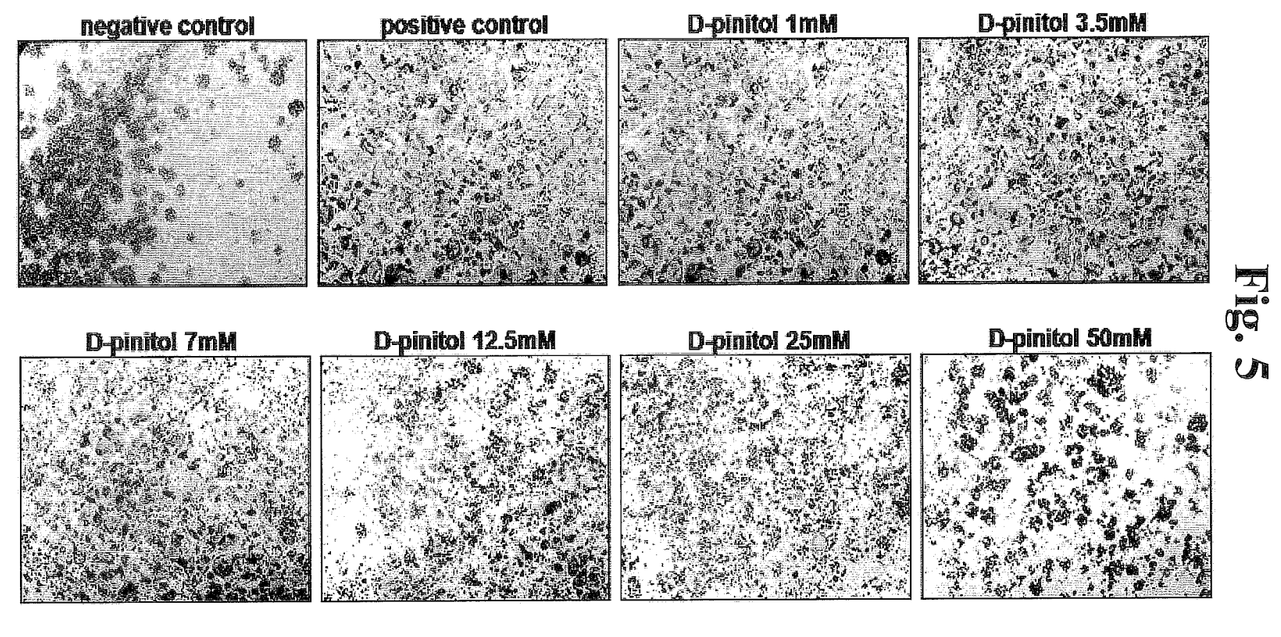
FIG. 5 is photographs representing the effects of D-pinitol on osteoclastogenesis of Raw 264.7 cell by TRAP staining. Raw 264.7 cells were treated with 200 ng/ml of RankL for 4 days and then osteoclastogenesis was confirmed at forth day by TRAP staining.

Raw264.7 cell line was treated with 200 ng/ml of RankL for 4 days. As shown in FIG. 5, osteoclastogenesis of Raw264.7 cell was not occurred when RankL was not added to Raw264.7 cell line (negative control). Fusion between cells was dramatically increased when 200 ng/ml of RankL was added to Raw264.7 cell line (positive control). Cells activated by RankL strongly exhibited scarlet color in TRAP staining and multinucleate cells, the fused cells, were observed.

To examine the effect of D-pinitol on the differentiation process of Raw264.7 cells, D-pinitol was added to the culture of Raw264.7 cells up to the concentration of 50 mM exhibiting no cytotoxicity, and then, osteoclastogenesis was observed. As shown in FIG. 5, osteoclastogenesis was significantly impaired according to the increase of the concentration of D-pinitol. The number of multinucleate cells observed in TRAP staining was also decreased according to the increase of the D-pinitol concentration. By these results, it could be found that D-pinitol is a substance to inhibit osteoclastogenesis.

Figure 6:
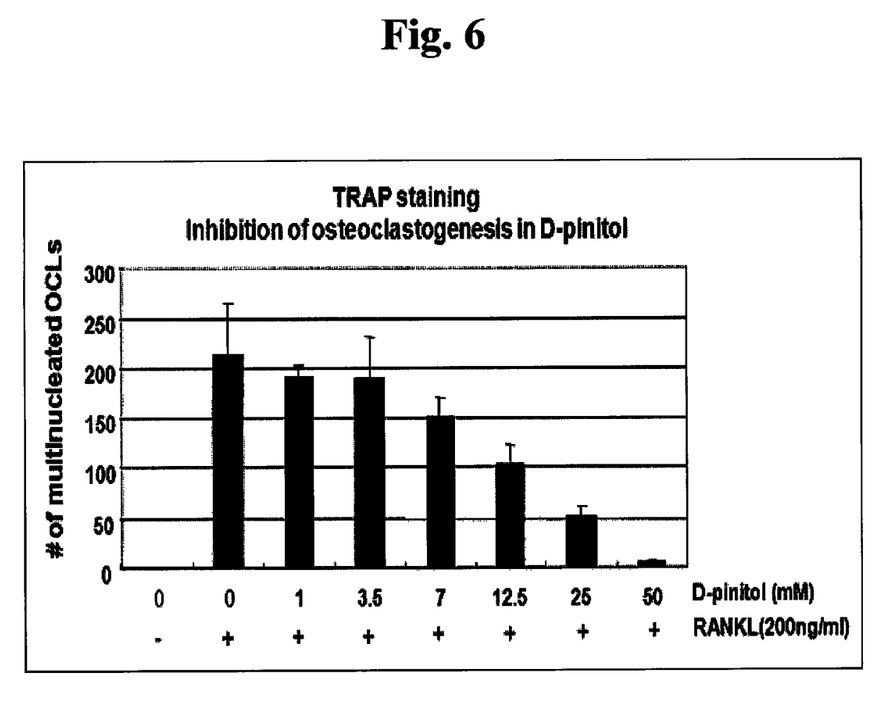
FIG. 6 is a graph showing the number of multinuclear osteoclast according to the treatment concentration of D-pinitol on osteoclastogenesis of Raw 264.7 cell using TRAP staining.

To quantitate inhibitory activity of D-pinitol in osteoclastogenesis of Raw264.7 cells, multinucleate cell number was measured via TRAP staining according to various treatment concentration of D-pinitol. As shown in FIG. 6, multinucleate cell number was significantly decreased according to the increase of the concentration of D-pinitol. Therefore, it could be understood that D-pinitol was a substance to inhibit osteoclastogenesis of Raw264.7 cell. D-pinitol inhibited osteoclastogenesis almost 100% at a concentration of 50 mM.

Figure 7:
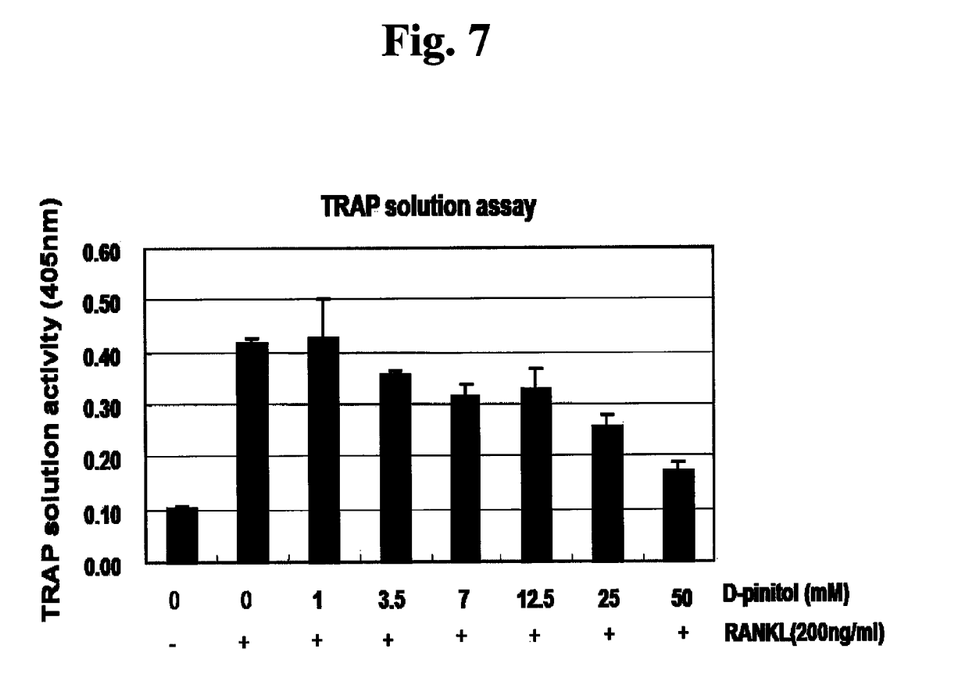
FIG. 7 is a graph showing the concentration-dependent effects of D-pinitol on osteoclastogenesis of Raw 264.7 cell by TRAP solution analysis.

Inhibitory Activity of D-pinitol on Osteoclastogenesis of Raw264.7 Cell—TRAP Solution Assay To investigate the inhibitory activity of D-pinitol in osteoclastogenesis of Raw264.7 cell, TRAP solution assay was carried out. TRAP (tartrate resistant acid phosphatase) was known to a typical marker protein in osteoclastogenesis. As shown in FIG. 7, the results obtained in TRAP solution assay were similar to those of TRAP staining, demonstrating the inhibitory activity of D-pinitol for osteoclastogenesis. However, the inhibitory activity of D-pinitol from TRAP solution assay was relatively weaker than that of one obtained by counting multinucleate cell number.

From these results, it could be suggested that the influence of D-pinitol on the conversion mechanism to TRAP positive cells was relatively weak in spite of the importance of TRAP as an osteoclast marker.

Inhibitory Activity of D-pinitol on Differentiation of Bone Marrow Derived Osteoclast—TRAP Staining Osteoclast is differentiated from monocytes in bone marrow. Bone marrow-derived osteoclast is a primary cell that is most close to osteoclast resides in the living body in contrast with Raw264.7 cells.

Progenitor cells of osteoclast were isolated from bone marrow and then used in the experiment of differentiation into osteoclast. Differentiated form of multinucleate cells can be observed in bone marrow-derived osteoclast via TRAP staining like Raw264.7 cells.

Figure 8:
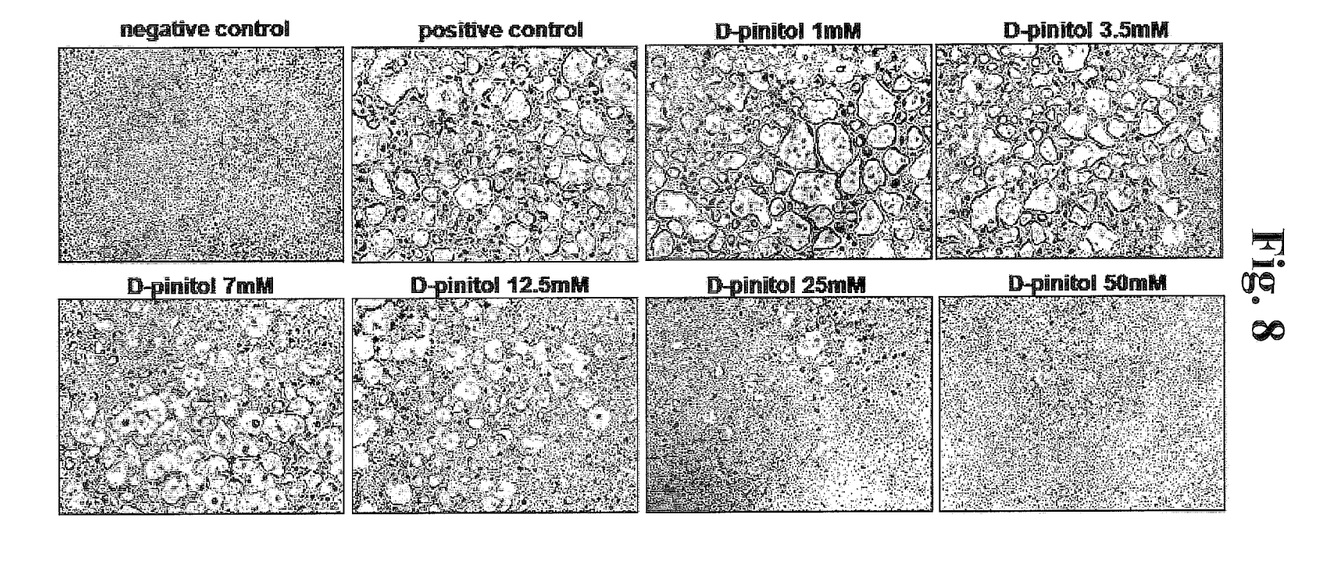
FIG. 8 is photographs representing the concentration-dependent effects of D-pinitol on the differentiation of bone marrow-derived osteoclast. Hematopoietic stem cells of bone marrow were incubated with 200 ng/ml of RankL and 50 ng/ml of CSF for 4 days and then osteoclastogenesis was confirmed at forth day via TRAP staining.

It could be confirmed as shown in FIG. 8 that osteoclast was formed at 4 days of culture when progenitor cells from bone marrow was cultured in the presence of RankL (200 ng/ml) and M-CSF (50 ng/ml) (positive control). However, osteoclast was not observed in cytokine-untreated cells (negative control).

To investigate the effect of D-pinitol on the osteoclast differentiation from bone marrow-derived monocyte, hematopoietic stem cells were extracted from bone marrow and activated for 1 day by M-CSF (5 ng/ml), resulting in induction of the differentiation into mononuclear cells. The mononuclear cells were cultured in the presence of 200 ng/ml of RankL and 50 ng/ml of M-CSF for 4 days. D-pinitol was added in a range of 0-50 mM during the culture and the differentiation pattern of osteoclast was observed using TRAP staining. As shown in FIG. 8, the number of TRAP-stained osteoclast was decreased in proportion to the concentration of D-pinitol, suggesting that D-pinitol inhibits the differentiation of bone marrow-derived osteoclast as similar to Raw264.7 cell.

Figure 9:
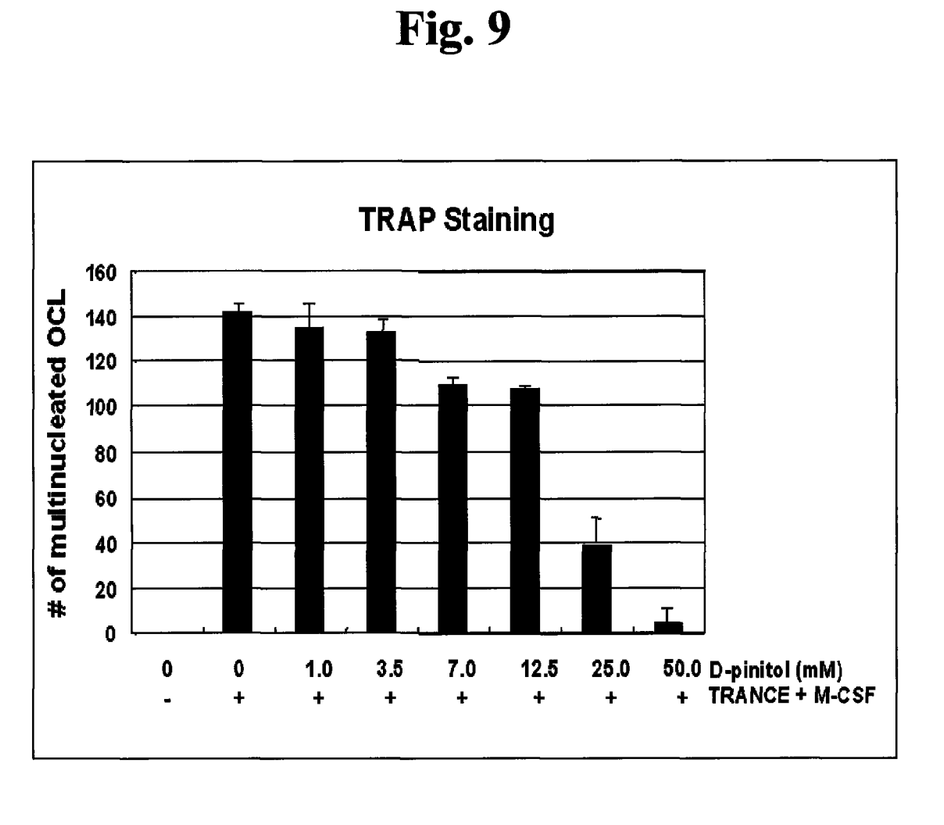
FIG. 9 is a graph representing the concentration-dependent effects of D-pinitol on multinucleation of bone marrow-derived osteoclast and osteoclastogenesis by TRAP staining.

To quantitate the effect of D-pinitol in osteoclatogenesis of bone marrow-derived monocyte, osteoclast cell number within sample was measured using TRAP staining. As shown in FIG. 9, the number of multinucleate cell was decreased according to the increase of D-pinitol concentration and a remarkable decrease was observed from 25 mM. D-pinitol at a concentration of 50 mM inhibited osteoclastogenesis almost up to 100%.

Figure 10:
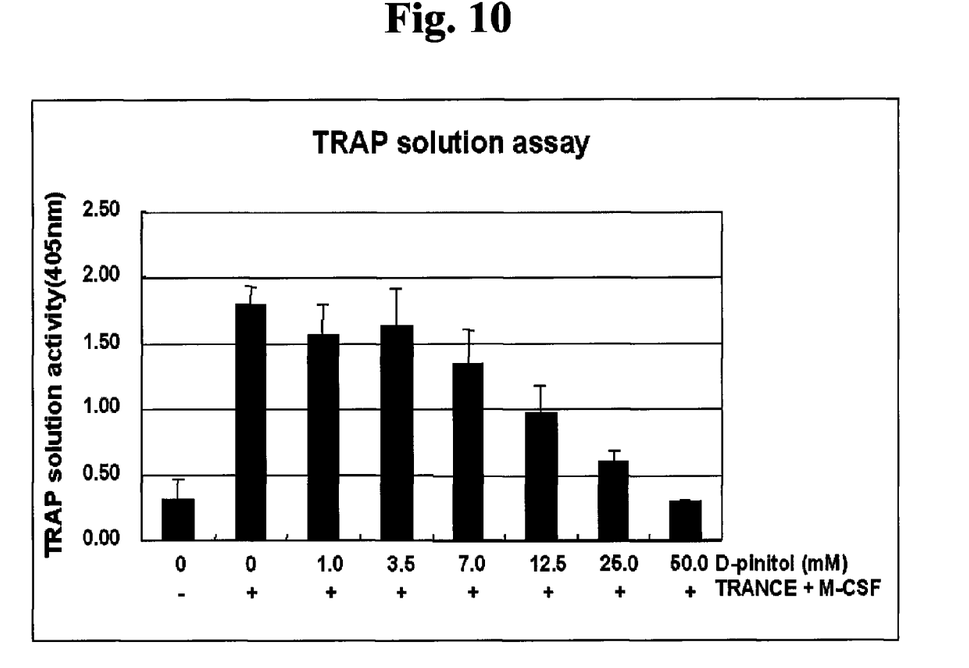
FIG. 10 is a graph representing the concentration-dependent effects of D-pinitol on multinucleation of bone marrow-derived osteoclast and osteoclastogenesis by TRAP solution analysis.

Inhibitory Activity of D-pinitol on Differentiation of Bone Marrow Derived Osteoclast—TRAP Solution Assay To determine inhibitory effect of D-pinitol on osteoclastogenesis, osteoclast derived from bone marrow primary cells was analyzed using TRAP solution assay. As shown in FIG. 10, the inhibitory effect on differentiation of bone marrow-derived osteoclast was also observed in the TRAP solution assay, suggesting that D-pinitol has an inhibitory effect on differentiation of bone marrow derived primary cells into TRAP positive cells.

Inhibitory Activity of D-pinitol on Osteoclastogenesis in Co-Culture of Osteoblast and Osteoclast Co-culture system of Osteoblast and Osteoclast is one that may provide the most similar environment to human body and allows us to study the process of osteoclastogenesis.

Figure 11:
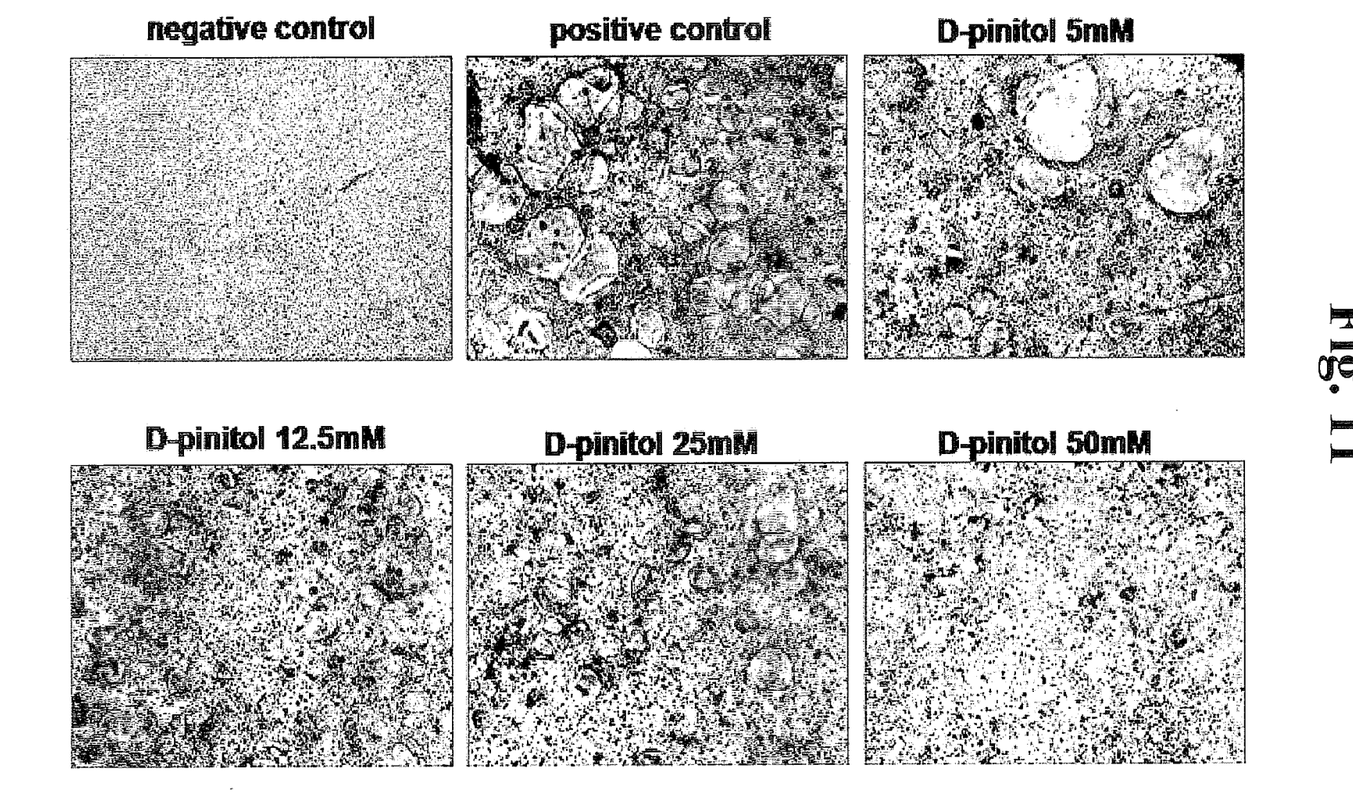
FIG. 11 is photographs representing the concentration-dependent effects of D-pinitol on osteoclastogenesis when osteoblast and bone marrow-derived osteoclast are co-cultured.

Osteoblast was extracted from mouse skull and then co-cultured with hematopoietic stem cells of bone marrow in order to induce the differentiation of osteoclast. The effect of D-pinitol on osteoclastogenesis was investigated by treating cells with D-pinitol with a range of 0-50 mM during the differentiation-inducing process. As shown in FIG. 11, the cell number of multinucleated osteoclast was significantly decreased according to the increase of the concentration of D-pinitol. Osteoclastogenesis was clearly inhibited at the concentration of 50 mM D-pinitol. From this result, it could be understood that D-pinitol also has an inhibitory effect on the differentiation of osteoclast in the co-culture system which is very similar to human body.

Figure 12:
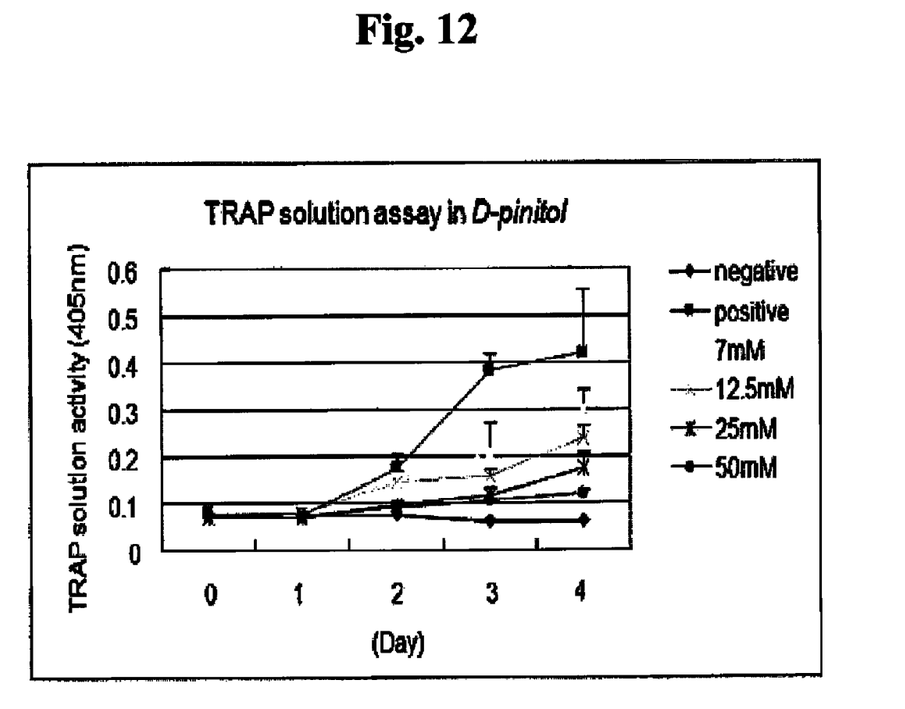
FIG. 12 is a graph representing the concentration-dependent effects of D-pinitol on each stage of the differentiation of bone marrow-derived osteoclast.

Inhibitory Activity of D-pinitol on Osteoclast Differentiation in Respective Stages of Osteoclastogenesis To analyze the effect of D-pinitol on respective stages of differentiation of bone marrow-derived osteoclast, the differentiation state of osteoclast, which has been cultured in the presence of various concentration of D-pinitol, was estimated in a time-dependent course. As shown in FIG. 12, multinucleate cell number of osteoclast was significantly decreased according to the increase of the concentration of D-pinitol. The differentiation of bone marrow-derived osteoclast was remarkably inhibited from 2 days after culture at not less than 25 mM of D-pinitol. The inhibitory activity of D-pinitol was clearly shown in osteoclastogenesis when it was treated at a concentration of 50 mM, which demonstrate that D-pinitol is a compound exerting an inhibitory effect at an early stage of osteoclastogenesis. It could be also understood that D-pinitol affects in the cell-fusion stage of the osteoclastogenesis.

Inhibitory Activity of D-pinitol on Bone Resorption and Degradation of Osteoclast Bone fragments were degraded and absorbed by osteoclasts in the body. Determination of bone resorption-degradative potential of osteoclast by using bone fragments is a suitable analysis method for estimating osteoclast function in vivo.

Figure 13:
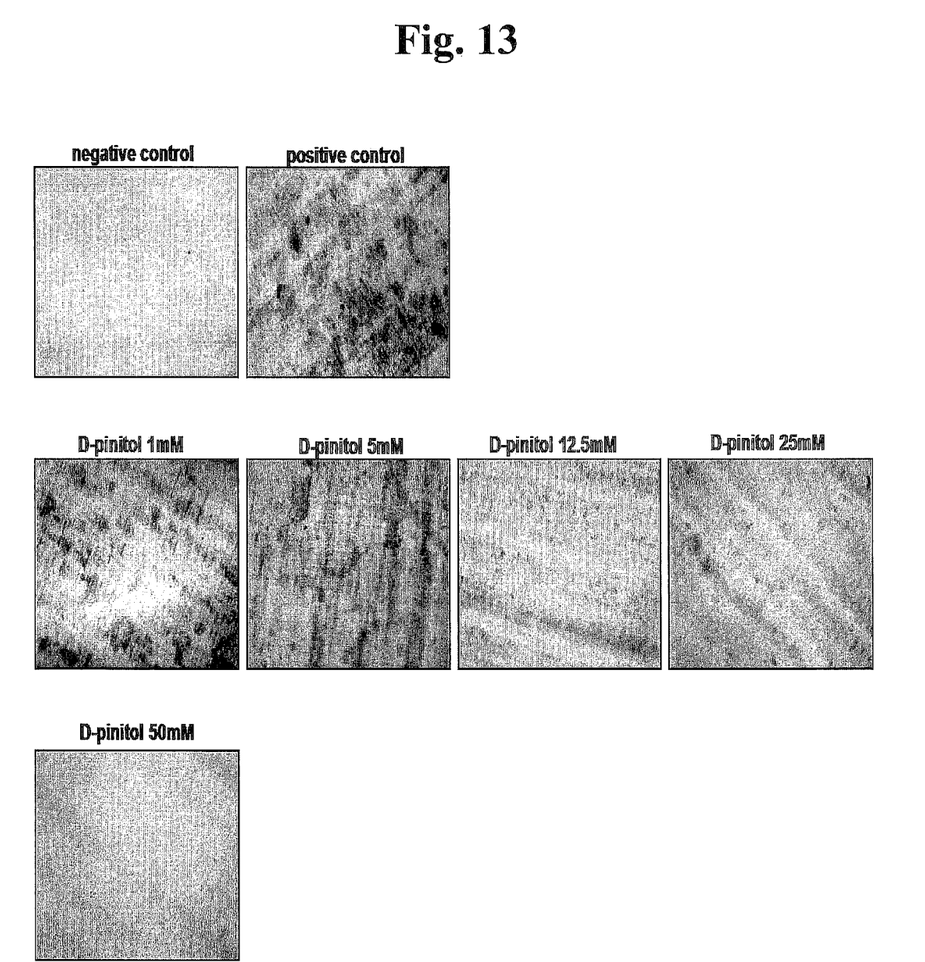
FIG. 13 is photographs representing the concentration-dependent effects of D-pinitol on bone absorption of bone marrow-derived osteoclast.

To investigate the effect of D-pinitol on the bone resorption-degradative potential of osteoclast, cells were treated with D-pinitol in the range of 0-50 mM during the differentiation into osteoclast on bone fragments which were obtained from human teeth. As shown in FIG. 13, it was confirmed by using bone staining assay that the bone resorption-degradative potential of osteoclast was remarkably decreased according to the increase of the concentration of D-pinitol. In particular, the bone resorption-degradative potential of osteoclast was dramatically decreased at the concentration of not less than 25 mM. This result demonstrates that the inhibition of osteoclastogenesis is related with that of bone resorption-degradative potential of osteoclast.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. TRANCE is a novel ligand of the tumor necrosis factor receptor family that activates c-Jun N-terminal kinase in T cells. J Biol Chem. 1997 Oct. 3; 272(40):25190-4.
2. Diverse roles of the tumor necrosis factor family member TRANCE in skeletal physiology revealed by TRANCE deficiency and partial rescue by a lymphocyte-expressed TRANCE transgene. Proc Natl Acad Sci USA. 2000 Sep. 26; 97(20):10905-10.
3. TRANCE, a TNF family member, activates Akt/PKB through a signaling complex involving TRAF6 and c-Src. Mol Cell. 1999 December; 4(6):1041-9.
4. Bisphosphonates: Mechanisms of Action. Endocr. Rev., February 1998; 19: 80-100.
5. The pathobiology of the osteoclast. J. Clin. Pathol., March 1985; 38: 241-252.
6. Cancer and Bone. Endocr. Rev., February 1998; 19: 18-54.

What is claimed is:

1. A method for treatment or inhibition of a bone metabolism disorder comprising administrating to a subject suffering from a bone metabolism disorder a pharmaceutical composition which comprises (a) a therapeutically effective amount of D-pinitol; and (b) a pharmaceutically acceptable carrier.

2. The method according to claim 1, wherein the bone metabolism disorder is osteoporosis, Paget's disease, hypercalcemia, neoplastic destruction, bone resorption disease associated with cancer, osteolysis, rheumatoid arthritis or immune disease.

* * * * *